US00PP11666P

United States Patent [19]

van Andel

[11] Patent Number: Plant 11,666

[45] Date of Patent: Dec. 5, 2000

[54] ALSTROEMERIA PLANT NAMED 'STALRA'

[75] Inventor: Jacob van Andel, Aalsmeer, Netherlands

[73] Assignee: Van Staaveren B.V., Aalsmeer, Netherlands

[21] Appl. No.: 09/226,319

[22] Filed: Jan. 6, 1999

[51] Int. Cl.[7] ..... A01H 5/00

[52] U.S. Cl. ..... Plt./309

[58] Field of Search ..... Plt./309

*Primary Examiner*—Howard J. Locker
*Attorney, Agent, or Firm*—Christie, Parker & Hale, LLP

[57] ABSTRACT

A new and distinct Alstroemeria plant variety producing flowers of good quality and attractive coloration.

1 Drawing Sheet

BACKGROUND OF THE INVENTION

The present invention relates to a new and distinct variety of Alstroemeria which is a cross of two unnamed, undistributed seedlings; namely, 82R473-6 as seed parent and 87G1069-2 as pollen parent. The varietal denomination of the new variety is 'Stalra'.

The first act of asexual reproduction of 'Stalra' was in Aalsmeer, The Netherlands, by propagation by dividing the rhizomes. Asexual reproduction by dividing rhizomes through successive generations in Aalsmeer, The Netherlands, has demonstrated that the combination of characteristics as herein disclosed for 'Stalra' are firmly fixed and retained through successive generations.

SUMMARY OF THE INVENTION

The new variety of Alstroemeria, 'Stalra', produces large flowers.

DESCRIPTION OF ILLUSTRATION

The new variety of Alstroemeria hybrid is illustrated in the accompanying illustration, which shows typical flower characteristics, with colors being as nearly true as is possible for illustration of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Colour Chart by color plate designations.

'Stalra' has not been observed under all possible environmental conditions. Phenotypic expression may vary with variations in environment such as temperature, light intensity, day length and growing and cultural conditions.

Botanical classification:
- *Family.*—Amaryllidaceae.
- *Genus.*—Alstroemeria sp.

Plant:
- *Form.*—Bush.
- *Shape.*—Upright.
- *Height.*—About 150 to 200 cm.
- *Main stem.*—About 180 cm.
- *Internode length.*—About 1–8 cm.
- *Growth.*—Vigorous.
- *Strength.*—Strong.
- *Blooming habit.*—Continuous.

- *Rhizomes.*—Plant about 1 to 2 years old. Color: Near 155D. Size: About 10 to 30 cm.

Foliage:
- *Number of leaves.*—About 20 to 45 per stem.
- *Size of leaf.*—Length: About 15 to 20 cm. Width: About 3 to 5 cm.
- *Shape of leaf.*—Elliptic.
- *Margin.*—Straight, entire.
- *Texture.*—Glossy.
- *Color.*—Upper side: Near 137A. Underside: Near 137C.

Flower:
- *Size (when first anthers release pollen).*—Diameter: About 7 cm. Depth: About 5 cm.
- *Borne.*—About 3 to 6 flowers per umbel.
- *Shape or form.*—When bloom first opens: Cup. When bloom matures: Cup.
- *Fragrance.*—None.
- *Lasting quality.*—On plant: About 4 weeks. As cut flower: About 18–20 days.
- *Tepalage.*—Number of tepals: About 6. Arrangement: 2 concentric circles of 3 tepals. Shape: Inner tepal long obovate, outer tepal obovate. Margin: Minutely crimped. Apex: Pointed. Texture: Soft. Appearance: Velvety.
- *Color.*—Outer tepals: Upper and under surface near 155A with some greenish striations, generally no spots. Inner lateral tepals: Upper surface — Base near 69D, body near 155A, about 20–30 spots, spots near 185A; Undersurface — Base near 69D, body near 155A. Inner median tepal: Upper surface — Base near 69D, body near 155A, about 5–15 spots, spots near 185A; Under surface — Base near 69D, body near 155A.
- *Peduncle length.*—About 10 to 15 cm. Color: Near 137B. Strength: Strong, erect.
- *Discoloration.*—No discoloration after full bloom, not hairy.
- *Persistence.*—Flower does not hang on and dry.
- *Disease resistance.*—Unknown.

Bud:
- *Size.*—Diameter: About 1 to 2 cm. Depth or length: About 2 to 4 cm.
- *Form.*—Pear-shaped.
- *Rate of opening.*—Fast.
- *Color of tepals when tepals first divide.*—Near 69D, 155A, and 138A.
- *Color of tepals when tepals begin to unfurl.*—Near 69D, 155A, and 138A.

Reproductive organs:

*Stamen.*—Number: About 6. Arrangement: Side by side around the style.

*Anthers.*—Size: About 8 to 10 mm. Color: Near 177B.

*Filaments.*—Length: About 5 cm. Color: Near 68B.

*Pollen.*—Color: Near 177B.

*Pistils.*—1. Styles: Length about 4 to 5 cm. Color: Near 68B.

*Stigmas.*—Color: Near 68B.

Fruit: Fertile.

*Shape.*—Round.

*Color at maturity.*—Near 163A.

I claim:

1. A new and distinct Alstroemeria plant of the variety substantially as shown and described.

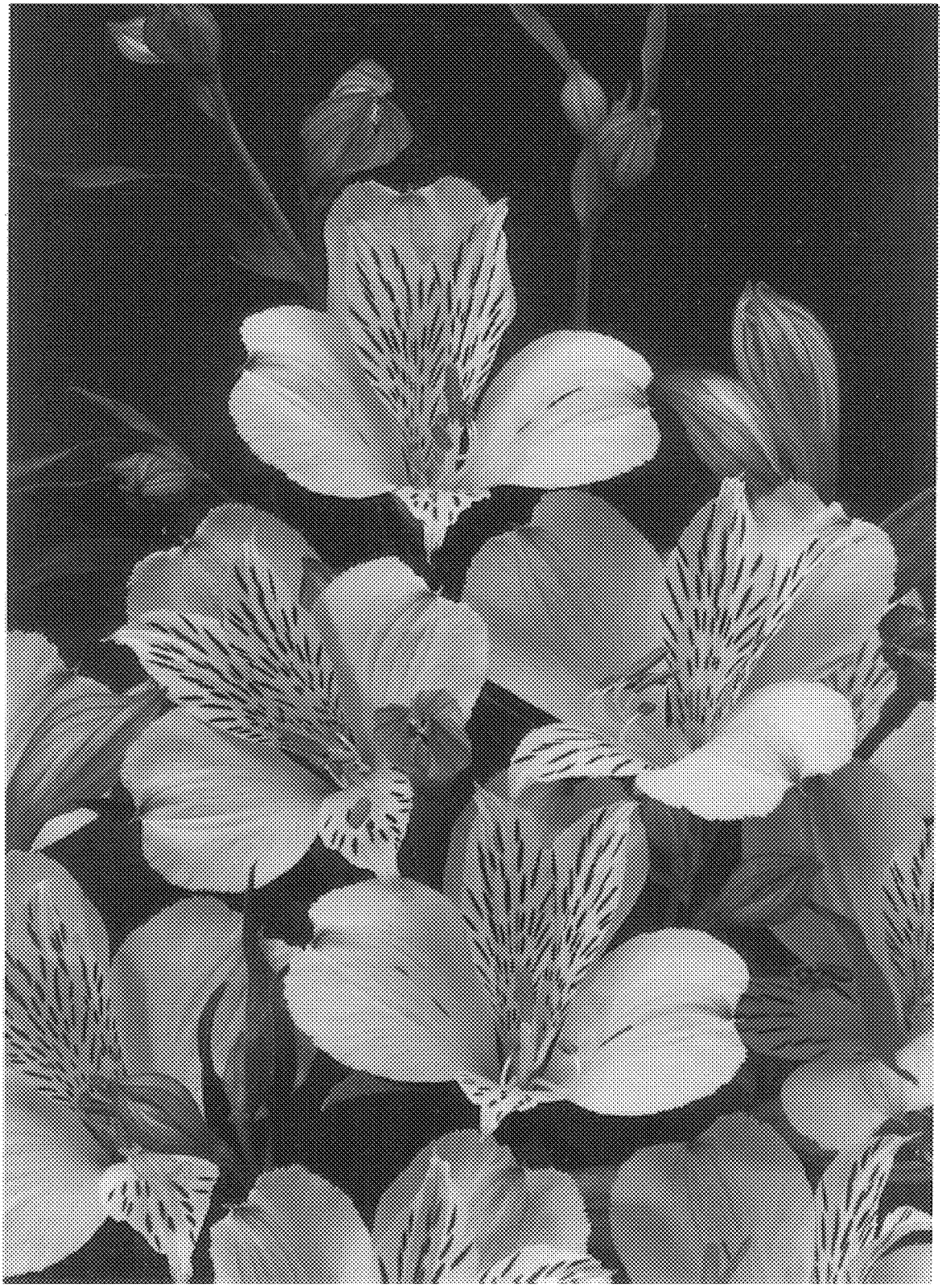

* * * * *